United States Patent [19]

Sullivan

[11] Patent Number: 5,144,063

[45] Date of Patent: Sep. 1, 1992

[54] USE OF HYDROXYTRIPHENYLBORATES TO PURIFY WASTE STREAMS

[76] Inventor: Jeffrey M. Sullivan, 1303 Carolina Ave., Longmont, Colo. 80501

[21] Appl. No.: 729,143

[22] Filed: Jul. 12, 1991

[51] Int. Cl.$^5$ .................................................. C07F 5/02
[52] U.S. Cl. ............................................ 562/7; 568/1; 568/6; 556/7; 534/10; 423/2; 423/184
[58] Field of Search ............... 562/7; 568/1, 6; 556/7; 534/10; 423/276, 277, 286, 2, 641, 249, 184

[56] References Cited

U.S. PATENT DOCUMENTS 4,689,437 8/1987 Murray ............................ 585/526
4,716,138 12/1987 Murray .............................. 568/13
4,822,915 4/1989 Murray .............................. 568/13

Primary Examiner—Stanley S. Silverman
Assistant Examiner—Neil M. McCarthy
Attorney, Agent, or Firm—Edward S. Irons

[57] ABSTRACT

Novel cesium hydroxytriphenylborates are described. The addition of hydroxytriarylborate ions to aqueous media containing cesium ions to form such compounds as a precipitate is useful, for example, in the removal of radioactive cesium from nuclear fission plant waste streams and from cesium ion containing solutions resulting from the digestion of cesium ores.

3 Claims, No Drawings

USE OF HYDROXYTRIPHENYLBORATES TO PURIFY WASTE STREAMS

FIELD OF INVENTION

This invention relates to certain novel cesium salts of hydroxytriarylborate. The invention also relates to the removal of radioactive cesium from waste streams by means of such salts and to the recovery of cesium in the form of such salts from cesium ores including pollucite.

BACKGROUND OF THE INVENTION

A more efficient procedure is needed for the removal of radioactive cesium from waste streams from nuclear fission plants. Present practice entails the addition of sodium tetraphenylborate to such streams with the consequent formation of a precipitate which must thereafter be disposed of. With some difficulty, the cesium component of the precipitate may be recovered.

Problems have also been encountered in the recovery of cesium from cesium ores, such as pollucite. Conventional technology involves digestion of the ore with sulfuric or hydrochloric acid to produce an acidic aqueous solution containing cesium ions. Cesium is recovered from such solutions in various ways. Alternatively, the cesium ore may be treated with a strong base to provide a basic solution containing cesium ions from which cesium is recovered.

SUMMARY OF THE INVENTION

This invention provides novel cesium salts of triarylmonohydroxyborates and cesium hydroxytris (4-chlorophenyl)borates.

Another aspect of the invention entails the discovery that these novel compounds are not significantly soluble in aqueous media at a pH above about 9.

Pursuant to yet another aspect of this invention, radioactive cesium present in nuclear fission plant waste streams is removed by precipitation as insoluble cesium hydroxytriphenylborate salts. Such salts then decompose, for example, in an aqueous solution at a pH of not more than about 6 to free the boron component for recycling.

Another aspect of the invention includes the recovery of cesium present in solutions derived from acidic or basic digestion of cesium ores by the addition of hydroxytriarylboron ions to precipitate a cesium salt thereof.

Hydroxytriarylboron ions may be provided either directly by the addition of sodium hydroxytriarylborate or by the addition of an aqueous solution containing from about 10 to 30% by weight of sodium hydroxytriarylborate to the medium from which it is desired to precipitate cesium hydroxytriarylborate.

DETAILED DESCRIPTION OF THE INVENTION

The novel compounds of the invention have the general formula

Cs B (X)3 OH in which X is any aryl group.

The aryl groups X may be the same or different, and may be phenyl, tolyl, or xylenyl groups. The aryl X groups may have substituents such as from about 1 to about 3 chlorine or bromine substituents.

Novel rubidium, potassium and lithium hydroxytriarylborates are included within the scope of the invention.

The preferred novel compound of the invention for use in processing cesium ores is cesium hydroxytriphenylborate having the formula:

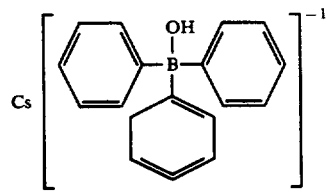

For use in the processing of waste streams from nuclear fission plants, it is preferred that the aryl groups tolyl or xylenyl aryl substituents or components of the hydroxytriarylborates are used to preclude the formation of benzene consequent from radiolysis.

Pursuant to the invention, it has been determined that the novel cesium salts of the invention including specifically cesium hydroxytriphenylborates are not significantly soluble in aqueous media having a pH greater than about 9.

These insoluble compounds may be synthesized in various ways, including specifically by the addition of cesium hydroxide to an aqueous solution of sodium hydroxytriphenylborate. Aqueous solutions containing from about 20% to about 30% sodium hydroxytriphenylborate are appropriate. Solid sodium hydroxytriphenylborates may be added directly to waste stream or cesium ore digestion solutions. Cesium hydroxytriphenylborate salts are precipitated selectively in the presence of other alkali metal and alkali earth metal ions.

EXAMPLE 3

A specimen of an aqueous waste stream from a nuclear fission plant which contains radioactive cesium and which is about 1.5 molar in hydroxyl content and about $2.5 \times 10^{-4}$ molar in cesium content is adjusted to a pH of at least about 9. An aqueous solution containing about 25% by weight of sodium hydroxytritolylborate is added with agitation. A precipitate of cesium hydroxytritolylborate is recovered. The precipitate is placed in an aqueous medium having a pH not less than about 5 and not greater than about 9 to liberate tritolylboron which may be recycled.

Waste streams from nuclear fission plants may be characterized by various pH levels. Hence, pH adjustment of the waste stream to a value of at least about 9 may be required in some cases for the practice of this invention.

EXAMPLE 2

An acidic aqueous medium containing cesium ions and obtained by the sulfuric acid digestion of pollucite ore is adjusted by the addition of aqueous sodium hydroxide solution to a pH of about 11. An aqueous solution containing about 25% by weight of sodium hydroxytriphenylborate is added to form a precipitate of cesium hydroxytriphenylborate. Cesium may be recovered from the precipitate when placed in an aqueous medium having a pH of not more than about 9.

I claim:

1. A compound having the formula

Cs B (X)3 OH in which X is any aryl group.
2. Cesium hydroxytriphenylborate.
3. Cesium hydroxytritolylborate.

* * * * *

UNITED STATES PATENT AND TRADEMARK OFFICE
CERTIFICATE OF CORRECTION

PATENT NO. : 5,144,063

DATED : September 1, 1992

INVENTOR(S) : Jeffrey M. Sullivan

It is certified that error appears in the above-identified patent and that said Letters Patent is hereby corrected as shown below:

Column 2, line 33, change "3" to --1--.

Signed and Sealed this

Twenty-sixth Day of October, 1993

*Attest:*

BRUCE LEHMAN

*Attesting Officer*     *Commissioner of Patents and Trademarks*